United States Patent [19]
Kitaoka

[11] Patent Number: 5,398,110
[45] Date of Patent: Mar. 14, 1995

[54] DIFFERENTIAL REFRACTOMETER

[75] Inventor: Mitsuo Kitaoka, Kyoto, Japan

[73] Assignee: Shimadzu Corporation, Kyoto, Japan

[21] Appl. No.: 40,451

[22] Filed: Apr. 1, 1993

[30] Foreign Application Priority Data

Apr. 9, 1992 [JP] Japan .................. 4-117952

[51] Int. Cl.$^6$ .......................................... G01N 21/41
[52] U.S. Cl. .................................................. 356/130
[58] Field of Search ............... 356/128, 130, 131, 132, 356/134

[56] References Cited

U.S. PATENT DOCUMENTS 3,674,373 7/1972 Waters et al. .................. 356/130

FOREIGN PATENT DOCUMENTS 250230 12/1985 Japan .................. 356/130

Primary Examiner—F. L. Evans
Attorney, Agent, or Firm—William L. Klima

[57] ABSTRACT

In order to satisfy both of high-sensitivity and low-sensitivity applications with no replacement of a flow cell, a photodetector (30) is divided into four portions (44-1, 44-2, 44-3, 44-4) by a first straight line (40) which is perpendicular to a direction of movement of a slit image (6) and a second straight line (42) which is inclined with respect to the direction of movement of the slit image (6) to intersect with the first straight line (40). Assuming that $S_1$, $S_2$, $S_3$ and $S_4$ represent intensity levels of detection signals of the photodetector portions respectively, the signals are processed along the following equations in analysis and preparative modes respectively:

$$Sa = c\{(S_2+S_3)-(S_1+S_4)\}/\{(S_2+S_3)+(S_1+S_4)]\}$$

$$Sp = c\{(S_1+S_2)-(S_3+S_4)\}/\{(S_1+S_2)+(S_3+S_4)]\}.$$

16 Claims, 5 Drawing Sheets

DIFFERENTIAL REFRACTOMETER

BACKGROUND OF THE INVENTION

1. Field of the Invention

The present invention relates to a differential refractometer which is employed as a detector for an analyzer, and a liquid chromatograph which is provided with such a differential refractometer as a detector.

2. Description of the Background Art

A differential refractometer is provided with a flow cell having two cells divided by a partition wall which is inclined with respect to an optical axis of a measuring beam. A sample solution passes through one of the cells, while a reference solution passes through or is held in the other cell. The differential refractometer further comprises a photodetector for receiving the measuring beam which is transmitted through and refracted by the flow cell, and an optical system for applying the measuring beam to the flow cell through a slit and guiding the measuring beam passing through the flow cell to the photodetector so that a slit image is formed on the photodetector. Change in refractive index of the sample solution is detected from the amount of displacement of the slit image on the photodetector.

As shown in FIG. 5A, a conventional differential refractometer is provided with a photodetector which is divided into two portions 2-1 and 2-2 by a straight line 4 being perpendicular to a direction X of movement of a slit image 6, to detect displacement of the slit image 6 on the photodetector. As the slit image 6 is moved toward the photodetector portion 2-2 upon increase in refractive index of a sample solution, a signal processing circuit performs the following operation and outputs the result:

$$S = C \cdot (s_2 - s_1)/(s_2 + s_1)$$

where $s_1$ and $s_2$ represent detection outputs of the photodetector portions 2-1 and 2-2 respectively, and C represents a constant. Assuming that the refractive index of the sample is changed by $\Delta n$ and the slit image 6 is moved in the direction X by a distance $\Delta x$, the above equation is transformed as follows:

$$\begin{aligned} S &= 2c \cdot \Delta x/d \\ &= 4cL \cdot \Delta n/d \end{aligned}$$

where c represents a span constant, L represents the distance between a flow cell and the photodetector, and d represents the width of the slit image 6. It is assumed that a partition wall of the flow cell is inclined at an angle of 45°. Thus, the output is proportional to the change in refractive index of the sample. On this photodetector, the signal is disadvantageously saturated if the overall slit image 6 enters the photodetector portion 2-2 as shown in FIG. 5B. In starting of measurement, therefore, it is necessary to locate the slit image 6 on a central portion across the straight line 4 separating the photodetector.

The differential refractometer is employed as a detector for an analyzer such as a liquid chromatograph, which is applied to two purposes of analysis and preparative use. When a highly sensitive differential refractometer for analysis is applied to preparative use, its signal is disadvantageously saturated due to a sample of relatively high concentration flowing a flow cell. In order to cope with this problem, therefore, generally employed is a flow cell having a partition wall which is varied in angle of inclination with analysis and preparative use. As an angle formed by the partition wall of such a flow cell and an optical axis of a measuring beam approaches 90°, the distance $\Delta x$ of movement of a slit image is reduced with respect to the same change in refractive index, to lower sensitivity.

A UV (ultraviolet) detector is also employed as a detector for a liquid chromatograph. Such a UV detector is provided with cassette type flow cell so that a flow cell for analysis can be easily replaced by that for preparative use or vice versa. In the differential refractometer, however, the overall optical system including the flow cell is temperature-controlled and hence it is difficult to replace the flow cell. The differential refractometer is also applicable to both purposes of analysis and preparative use since its sensitivity can be varied with the angle of the partition wall dividing the cells. In general, however, different chromatographs are independently applied to analysis and preparative use since it is difficult to replace the flow cell. In order to solve this problem, Japanese Patent Laying-Open Gazette No. 63-27733 (1988) describes a detector comprising a light emitting diode serving as a light source, a condenser lens which is interposed between this light source and a slit, a flow cell which is divided into a sample cell and a reference cell having independent passages respectively, and a PSD (semiconductor position detector) for serving as a photodetector portion. However, the PSD employed in this detector is unsuitable for analysis due to a large noise.

A flow cell of a differential refractometer comprises a sample cell and a reference cell. A narrow pipe of 0.25 to 0.5 mm in inner diameter is provided as a conduit on an inlet side of the sample cell, to prevent reduction of separation by its column. On the other hand, an outlet side of the sample cell and inlet and outlet sides of the reference cell are not particularly restricted and conduits therefor are prepared from pipes which are larger in thickness than that provided on the inlet side of the sample cell.

In order to apply a differential refractometer to two purposes of analysis and preparative use, the following two points are required:

(a) A detection signal must not be saturated up to a high concentration region since a sample of high concentration flows into the cell at a high velocity in preparative use.

(b) Thick pipes must be provided on inlet and outlet sides of the cells in preparative use.

While it is possible to satisfy the point (b) by changing connection of flow lines so that a cell serving as a reference cell in analysis in turn serves as a sample cell in preparative use, it is impossible to satisfy the point (a). As the result, different detectors are independently required for analysis and preparative use. Thus, a detector having a partition wall which is inclined at an angle of 45° is applied to analysis, while that having a partition wall which is inclined at an angle of 6° to 12° is applied to preparative use.

SUMMARY OF THE INVENTION

An object of the present invention is to provide a differential refractometer which is employable for both of high-sensitivity and low-sensitivity applications such as analysis and preparative use through a photodetector and a signal processing circuit being connected therewith, with no replacement of a flow cell.

Another object of the present invention is to provide a liquid chromatograph comprising such a differential refractometer, which has two functions of analysis and preparative use.

In order to enable switching between high-sensitivity and low-sensitivity applications, a photodetector provided in the inventive differential refractometer is divided by a first straight line which is perpendicular to a direction of movement of a slit image and a second straight line which is inclined with respect to the direction of movement of the slit image to intersect with the first straight line, to utilize difference between outputs of photodetector portions holding the first straight line with the slit image being located across the first straight line for high-sensitivity detection while utilizing difference between outputs of other photodetector portions holding the second straight line with the slit image being located across the second straight line for low-sensitivity detection.

Thus, it is possible to switch high sensitivity detection and low sensitivity detection only by processing a detection signal from a photodetector which is contained in a single apparatus, with no operation such as replacement of a flow cell or the photodetector.

The inventive liquid chromatograph comprises the aforementioned differential refractometer, to serve both functions of analysis and preparative use by changing connection of flow lines of sample and reference cells in analysis and preparative use.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
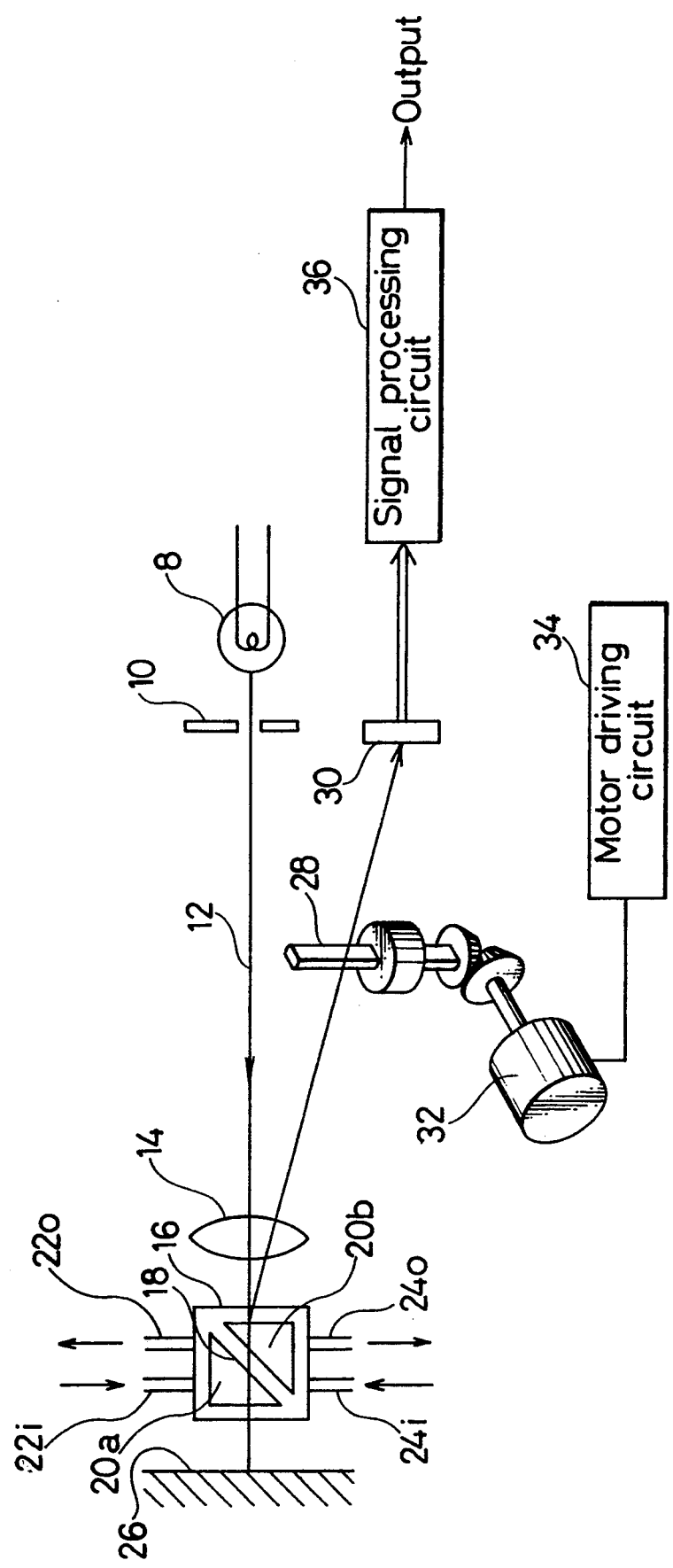
FIG. 1 is a block diagram schematically showing a differential refractometer according to an embodiment of the present invention.

FIG. 1 schematically illustrates a differential refractometer according to an embodiment of the present invention. Referring to FIG. 1, light emitted from a light source 8 passes through a slit 10 to form a measuring beam 12, which in turn is applied to a flow cell 16 through a lens 14 provided in front of the flow cell 16. The flow cell 16 comprises two cells 20a and 20b which are divided by a partition wall 18. The cell 20a has an inlet port 22i and an outlet port 22o for a solution, while the cell 20b has an inlet port 24i and an outlet port 24o for another solution. A mirror 26 is arranged at the back of the flow cell 16. The measuring beam 12 which is transmitted through the flow cell 16 is reflected by this mirror 26, to be transmitted through the flow cell 16 again. The measuring beam 12 thus transmitted through the flow cell 16 and reflected by the mirror 26 forms a slit image on a photodetector 30 through the lens 14.

In order to move the slit image formed on the photodetector 30 along the direction of movement of the slit image based on change in refractive index at the flow cell 16, a zero glass 28 is arranged on the optical path of the measuring beam 12. The zero glass 28 can move the slit image formed on the photodetector 30 by a pulse motor 32 which is driven by a motor driving circuit 34, or through a manual operation. A signal processing circuit 36 performs signal processing for obtaining the change in refractive index on the basis of a detection signal from the photodetector 30.

In the flow cell 16, the inlet port 22i of the cell 20a is set at 0.25 mm to 0.3 mm in inner diameter, while the outlet port 22o of the cell 20a and the inlet and outlet ports 24i and 24o of the other cell 20b are set at 0.3 mm to 1.0 mm in inner diameter respectively.

Figure 2A:
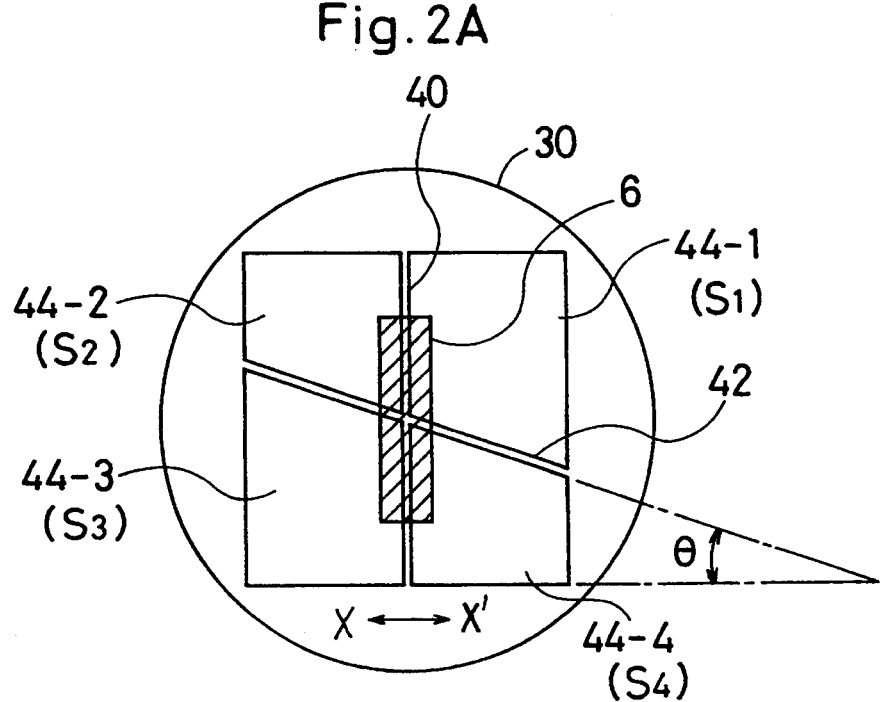
FIG. 2A is a front elevational view showing a position of a slit image in starting of measurement in an analysis mode of a photodetector in the differential refractometer according to the embodiment of the present invention.

As shown in FIG. 2A, the photodetector 30 is divided into four portions 44-1, 44-2, 44-3 and 44-4 by a first straight line 40 which is perpendicular to a direction of movement of a slit image 6 and a second straight line 42 which is inclined with respect to the direction of movement of the slit image 6 to intersect with the first straight line 40. It is assumed that $S_1$ to $S_4$ represent photoelectric current levels of detection signals of the respective photodetector portions 44-1 to 44-4, and $\theta$ represents an angle of inclination of the second straight line 42 with respect to the direction of movement of the slit image 6.

Operations of this embodiment are now described.

Analytical Mode

When the differential refractometer is employed for analysis, the cells 20a and 20b of the flow cell 16 are applied to sample and reference uses respectively. In starting of measurement, the zero glass 28 locates the slit image 6 at a central position across the straight line 40, as shown in FIG. 2A.

As the slit image 6 is leftwardly (X direction) moved in FIG. 2A upon increase in refractive index of a sample solution, the signal processing circuit 36 operates the detection signals of the photodetector portions 44-1 to 44-4 and outputs the same as follows:

$$Sa = c\{(S_2+S_3)-(S_1+S_4)\}/\{(S_2+S_3)+(S_1+S_4)\}$$

This is the same usage as a conventional differential refractometer. Assuming that the partition wall 18 of the flow cell 16 is inclined at 45°, for example, the above equation is transformed as follows:

$$Sa = 4cL \cdot \Delta n/d$$

Preparative Mode

When the differential refractometer is employed for preparative use, connection of flow lines is so changed that the cell 20b having the thick inlet and outlet ports 24i and 24o is applied to a sample use while the cell 20a is applied to a reference use in the flow cell 16, since a sample flows into the refractometer at a high velocity. When the refractive index is increased on the cell 20b side in this case, the slit image 6 is moved in a direction opposite to that in analysis. Namely, the slit image 6 is rightwardly (X' direction) moved in FIG. 2B.

In such preparative use, the signal processing circuit 36 performs the following operation and outputs the result:

$$Sp = c\{(S_1+S_2)-(S_3+S_4)\}/\{(S_1+S_2)+(S_3+S_4)\}$$

Assuming that the partition wall 18 of the flow cell 16 is inclined at an angle of 45°, the above equation is transformed as follows:

$$Sp = 4c \cdot \tan\theta \cdot \Delta n \cdot L/h$$

A signal attenuation factor Sp/Sa is as follows:

$$Sp/Sa = d \cdot \tan\theta/h$$

Assuming that the slit image 6 has a width d of 0.5 mm and a height h of 4 mm and the straight line 42 is inclined at an angle $\theta$ of 15°, the signal attenuation factor is about 1/30. This means that sensitivity is reduced to about 1/30.

Figure 2B:
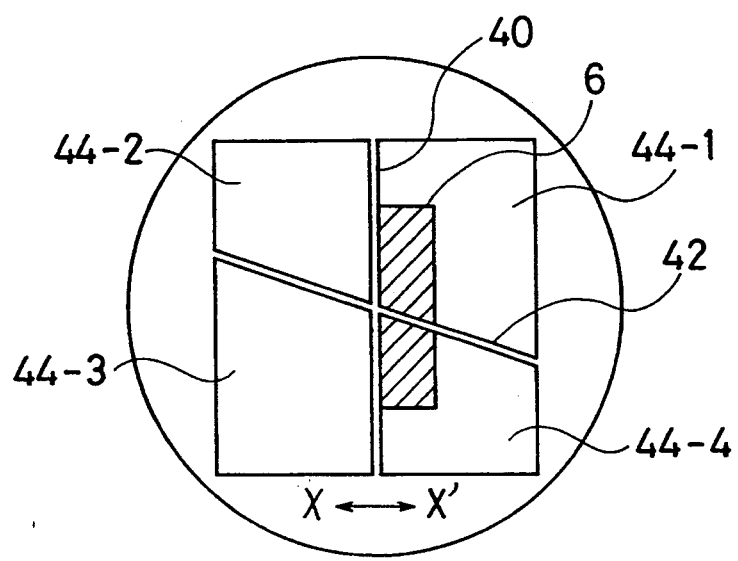
FIG. 2B is a front elevational view showing a position of the slit image in starting of measurement in a preparative mode of the photodetector.

Since the signal is not saturated until the slit image 6 reaches an end of the photodetector 30 in FIG. 2B, it is possible to perform measurement to a high concentration region by increasing a lateral width of the photodetector 30 and reducing the angle $\theta$ of inclination of the straight line 42.

Since the straight line 40 has a finite width, linearity is not maintained in principle when the slit image 6 passes through the straight line 40 in the preparative mode. In starting of measurement, therefore, the slit image 6 may be previously moved by the zero glass 28 to wholly enter the photodetector portions 44-1 and 44-4 as shown in FIG. 2B, so that movement of the slit image 6 is monitored from this position being regarded as a start position. In this case, signal processing may be performed along the following equation:

$$Sp = c(S_1-S_4)/(S_1+S_4)$$

When the refractive index is reduced with respect to the reference side, on the other hand, the slit image 6 is moved in the opposite direction and hence the measurement start position may be moved toward the photodetector portions 44-2 and 44-3.

As to such movement of the slit image 6 toward the starting position for measurement, the zero glass 28 may be manually operated or the same may be automated by the pulse motor 32 to move the slit image 6 to a constant position.

A liquid chromatograph according to another embodiment of the present invention, employing the aforementioned differential refractometer as a detector, is now described.

Figure 3:
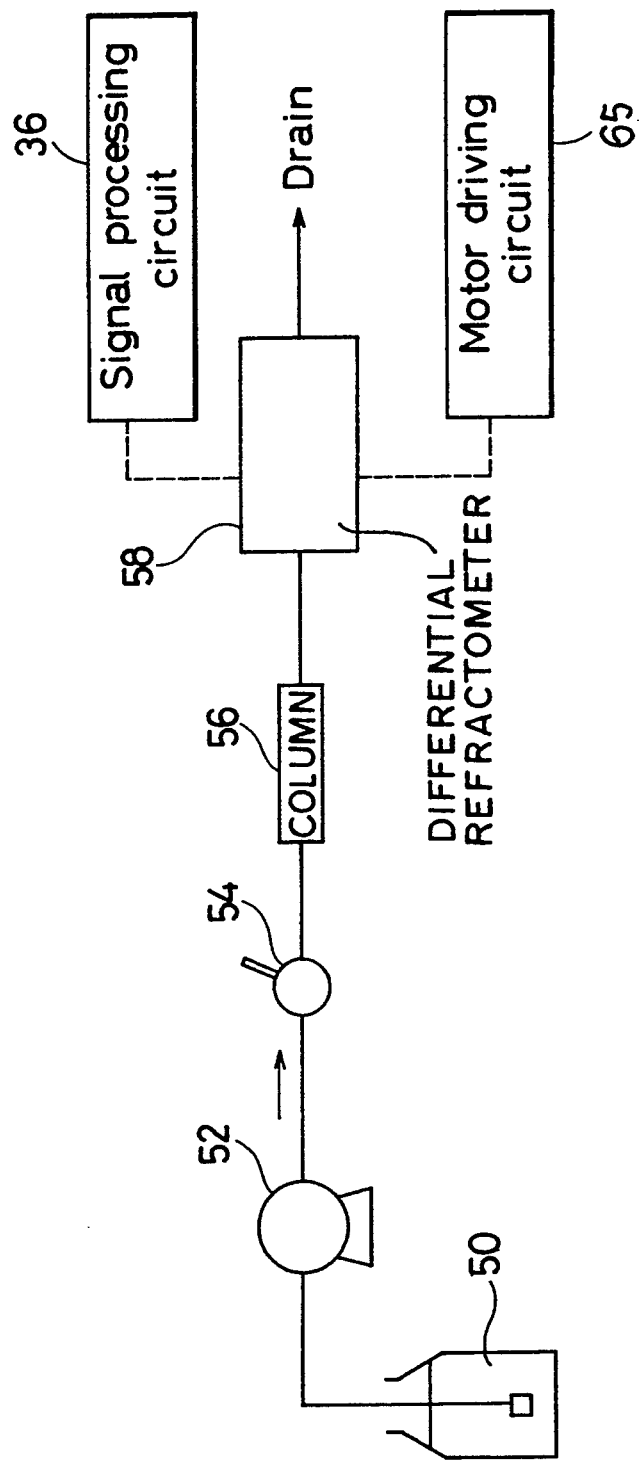
FIG. 3 is a flow diagram showing a liquid chromatograph according to another embodiment of the present invention.

FIG. 3 illustrates the inventive liquid chromatograph. A sample injector 54 is provided in a flow line for feeding an eluent 50 to a column 56 by a feed pump 52, to inject a sample. An effluent from the column 56 flows to a differential refractometer 58, which is identical to that described above with reference to FIGS. 1, 2A and 2B, to be subjected to analysis and preparative use. The as-analyzed effluent or a part of the effluent unnecessary for fraction collecting is discharged to a drain.

Figure 4A:
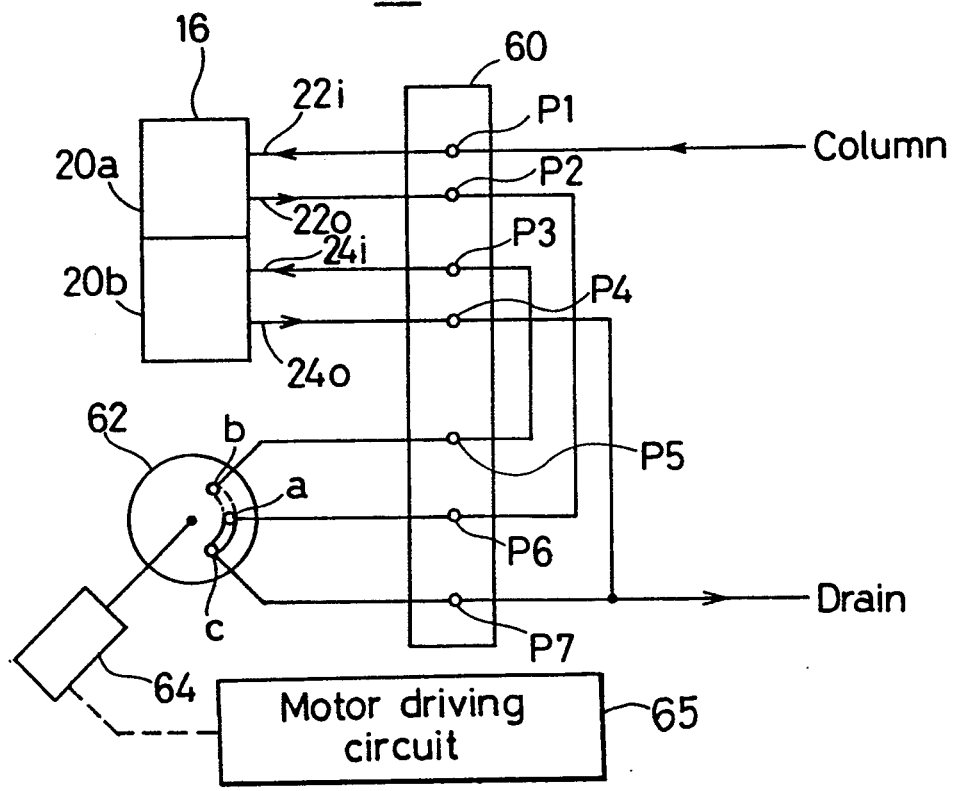
FIG. 4A is a flow diagram showing connection of flow lines in an analysis mode in the liquid chromatograph.
Figure 4B:
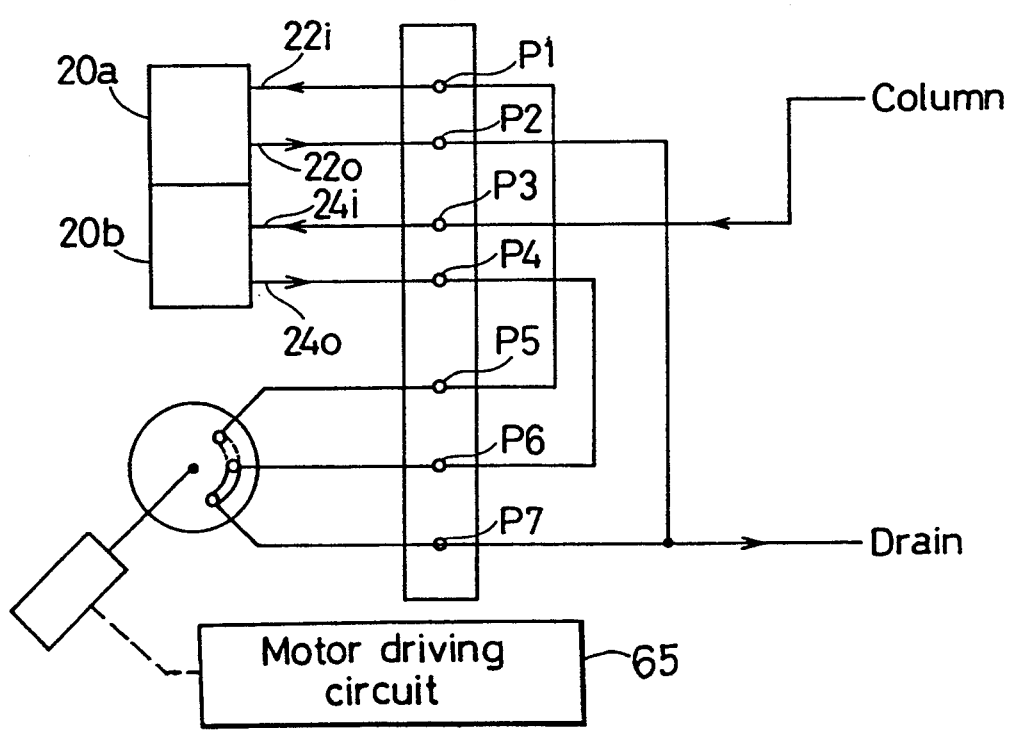
FIG. 4B is a flow diagram showing connection of flow lines in a preparative mode in the liquid chromatograph.
Figure 5A:
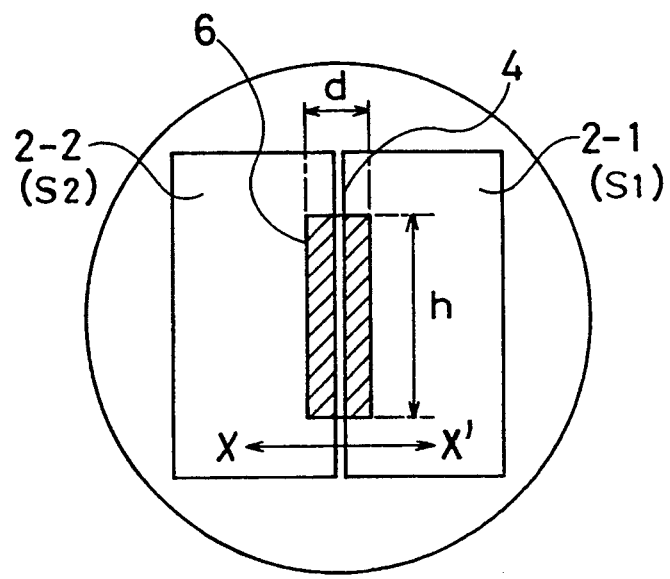
FIG. 5A is a front elevational view showing a position of a slit image in starting of measurement of a photodetector in a conventional differential refractometer.
Figure 5B:
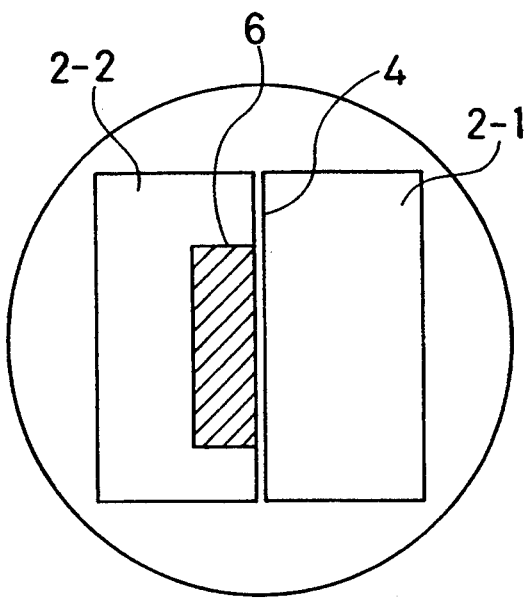
FIG. 5B is a front elevational view showing a saturated state of a signal in the photodetector.

The differential refractometer 58 is provided with flow line switching means for a flow cell as shown in FIGS. 4A and 4B, in a portion excluding the motor driving circuit 65 and the signal processing circuit 36.

This flow line switching means is now described with reference to FIG. 4A showing flow lines in an analysis mode. A three-way valve 62 is provided in order to guide the eluent to a reference cell as a reference solution. The three-way valve 62, which is provided with one inlet port a and two outlet ports b and c, is driven by a motor 64 so that the inlet port a can be connected to either the outlet port b or c. Inlet and outlet ports 22i, 22o, 24i and 24o of a flow cell 16 and the inlet and outlet ports a, b and c of the three-way valve 62 are connected to independent ports P1 to P7 of a joint portion 60 respectively. As to these ports P1 to P7, it is possible to freely change connection between the ports, that between the ports and the column 56, and that between the ports and the drain.

In the analysis mode, cells 20a and 20b of the flow cell 16 are applied to sample and reference uses respectively as shown in FIG. 4A. The flow line from the column 56 is connected to the inlet port 22i of the cell 20a of the flow cell 16 through the port P1 of the joint portion 60. This inlet port 22i of the cell 20a has smaller volume than the other ports 22o, 24i and 24o. On the other hand, the outlet port 22o of the cell 20a is connected to the inlet port a of the three-way valve 62 through the port P2, a flow line and the port P6. The outlet port b of the three-way valve 62 is connected to the inlet port 24i of the cell 20b through the port P5, a flow line and the port P3, while the outlet port 24o of the cell 20b is connected to the drain through the port p4. The outlet port c of the three-way valve 62 is connected to the drain through the port P7.

In the analysis mode, the three-way valve 62 is switched to connect the inlet port a with the outlet port b before the analysis operation, so that the eluent flowing out of the column 56 passes through the cell 20b via the cell 20a and the three-way valve 62, to be discharged to the drain. Thereafter the three-way valve 62 is switched to connect the inlet port a with the outlet port c, whereby the effluent from the column 56 passes only through the cell 20a, to be detected by the cell 20a. A part of the eluent precedently flowing in the cell 20b remains therein as a reference solution.

FIG. 4B shows flow lines in a preparative mode. Passage connection in the joint portion 60 is so switched that the cells 20b and 20a are in turn applied to sample and reference uses respectively. The flow line from the column 56 is connected to the cell 20b through the port P3, while the outlet port 24o of the cell 20b is connected to the inlet port a of the three-way valve 62 through the port P4, a flow line and the port P6. The outlet port b of the three-way valve 62 is connected to the inlet port 22i of the cell 20a through the port P5, a flow line and the port P1, while the outlet port 22o of the cell 20a is connected to the drain through the port P2. The outlet port c of the three-way valve 62 is connected to the drain.

Also in the preparative mode, the eluent flowing out of the column 56 before starting of the preparative operation flows from the cell 20b to the cell 20a through the three-way valve 62. Thereafter the three-way valve 62 is so switched that the eluent remains in the cell 20a as a reference solution. In the preparative operation, an effluent flows into the cell 20b from the column 56 to be detected therein, and the fraction is collected before the same is discharged to the drain.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A differential refractometer, comprising:
   a flow cell having two cells divided by a partition wall being inclined with respect to an optical axis of a measuring beam, so that a sample solution passes through one of said two cells and a reference solution passes through or is held in the other said cell;
   an optical system for transmitting said measuring beam passing through a slit through said flow cell, reflecting said transmitted measuring beam by a mirror for transmitting said measuring beam through said flow cell again and thereafter making said measuring beam from said flow cell form a slit image on a photodetector;
   said photodetector being divided into four portions by a first straight line being perpendicular to a direction of movement of said slit image and a second straight line being inclined with respect to said direction of movement of said slit image to intersect with said first straight line; and
   an operation part receiving output signals from said divided portions of said photodetector for calculating difference between outputs of said photodetector portions divided by said first straight line with said slit image being located across said first straight line for high-sensitivity detection, while calculating difference between outputs of said photodetector portions divided by said second straight line with said slit image being located across said second straight line for low-sensitivity detection.

2. A differential refractometer in accordance with claim 1, further comprising slit image moving means being provided between said flow cell and said photodetector for moving said slit image formed on said photodetector in said direction of movement of said slit image for setting an initial position of said slit image on said photodetector.

3. A differential refractometer in accordance with claim 2, wherein
   said initial position of said slit image is set across said second straight line on one side of said first straight line which is perpendicular to said direction of movement of said slit image by change in refractive index in said flow cell.

4. A differential refractometer in accordance with claim 1, further comprising first flow line switching means being provided between said two cells of said flow cell for switching a flow line for discharging a solution from a sample cell through a reference cell and a flow line for discharging said solution directly from said sample cell,
   said first flow line switching means switching said flow lines so that said solution from said sample cell flows also to said reference cell in advance of starting of an analysis or preparation operation and said solution does not flow to said reference cell after said starting of said analysis or preparation operation so that a part of said solution remaining in said reference cell serves as a reference solution.

5. A differential refractometer in accordance with claim 4, wherein
   said first flow line switching means is a rotary valve.

6. A differential refractometer in accordance with claim 1, wherein
   one of said two cells of said flow cell has an inlet port being smaller in diameter than that of the other said cell,
   said differential refractometer further comprising flow line switching means for switching flow lines so that said cell having said inlet port of a smaller diameter serves as a sample cell and the other said cell serves as a reference cell in an analysis mode while the former serves as a reference cell and the latter serves as a sample cell in a preparative mode.

7. A differential refractometer in accordance with claim 6, wherein
   said flow line switching means is a joint portion capable of changing connection of said flow lines.

8. A differential refractometer in accordance with claim 1, wherein
   one of said two cells of said flow cell has an inlet port being smaller in diameter than that of the other said cell,
   said differential refractometer further comprising a rotary valve having a solution inlet port and two solution outlet ports being selectively connected to said solution inlet port, and
   a joint portion having ports being connected to respective said inlet and outlet ports of said two cells and said solution inlet port and said solution outlet ports of said rotary valve respectively, said joint portion being capable of varying connection between said ports and that between said ports and an external flow line.

9. A liquid chromatograph having a flow line for feeding an eluent to a column by a feed pump, a sample injector provided in said flow line and a differential refractometer as a detector provided in another flow line connecting an outlet of said column with a drain, said differential refractometer comprising:
   a flow cell having two cells divided by a partition wall being inclined with respect to an optical axis of a measuring beam, so that a sample solution passes through one of said two cells and a reference solution passes through or is held in the other said cell;
   an optical system for transmitting said measuring beam passing through a slit through said flow cell, reflecting said transmitted measuring beam by a mirror for transmitting said measuring beam through said flow cell again and thereafter making said measuring beam from said flow cell form a slit image on a photodetector;
   said photodetector being divided into four portions by a first straight line being perpendicular to a direction of movement of said slit image and a second straight line being inclined with respect to said direction of movement of said slit image to intersect with said first straight line; and an operation part receiving output signals from respective said divided portions of said photodetector for calculating difference between outputs of said photodetector portions divided by said first straight line with said slit image being located across said first straight line for high-sensitivity detection, while calculating difference between outputs of said photodetector portions divided by said second straight line with said slit image being located across said second straight line for low-sensitivity detection.

10. A liquid chromatograph in accordance with claim 9, further comprising slit image moving means being provided between said flow cell and said photodetector for moving said slit image formed on said photodetector in said direction of movement of said slit image for setting an initial position of said slit image on said photodetector.

11. A liquid chromatograph in accordance with claim 10, wherein
said initial position of said slit image is set across said second straight line on one side of said first straight line which is perpendicular to said direction of movement of said slit image by change in refractive index in said flow cell.

12. A liquid chromatograph in accordance with claim 9, further comprising first flow line switching means being provided between said two cells of said flow cell for switching a flow line for discharging a solution from a sample cell through a reference cell and a flow line for discharging said solution directly form said sample cell,
said first flow line switching means switching said flow lines so that said solution from said sample cell flows also to said reference cell in advance of starting of an analysis or preparation operation and said solution does not flow to said reference cell after said starting of said analysis or preparation operation so that a part of said solution remaining in said reference cell serves as a reference solution.

13. A liquid chromatograph in accordance with claim 12, wherein
said first flow line switching means is a rotary valve.

14. A liquid chromatograph in accordance with claim 9, wherein
one of said two cells of said flow cell has an inlet port being smaller in diameter than that of the other said cell,
said differential refractometer further comprising flow line switching means for switching flow lines so that said cell having said inlet port of a smaller diameter serves as a sample cell and the other said cell serves as a reference cell in an analysis mode while the former serves as a reference cell and the latter serves as a sample cell in a preparative mode.

15. A liquid chromatograph in accordance with claim 14, wherein
said flow line switching means is a joint portion capable of changing connection of said flow lines.

16. A liquid chromatograph in accordance with claim 9, wherein
one of said two cells of said flow cell has an inlet port being smaller in diameter than that of the other said cell,
said differential refractometer further comprising a rotary valve having a solution inlet port and two solution outlet ports being selectively connected to said solution inlet port, and
a joint portion having ports being connected to respective said inlet and outlet ports of said two cells and said solution inlet port and said solution outlet ports of said rotary valve respectively, said joint portion being capable of varying connection between said ports, that between said ports and said outlet of said column and that between said ports and said drain.

* * * * *